United States Patent
Rosenzweig et al.

(10) Patent No.: US 11,311,275 B2
(45) Date of Patent: Apr. 26, 2022

(54) ASYMMETRY FOR ACOUSTIC RADIATION FORCE IMPULSE

(71) Applicant: Siemens Medical Solutions USA, Inc., Malvern, PA (US)

(72) Inventors: Stephen J. Rosenzweig, Seattle, WA (US); Paul Reynolds, Renton, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 329 days.

(21) Appl. No.: 16/367,296

(22) Filed: Mar. 28, 2019

(65) Prior Publication Data
US 2020/0305842 A1  Oct. 1, 2020

(51) Int. Cl.
*A61B 8/00* (2006.01)
*A61B 8/08* (2006.01)
*G01S 15/62* (2006.01)

(52) U.S. Cl.
CPC ........... *A61B 8/485* (2013.01); *A61B 8/483* (2013.01); *A61B 8/5207* (2013.01); *G01S 15/62* (2013.01)

(58) Field of Classification Search
CPC ....... A61B 8/485; A61B 8/483; A61B 8/5207; G01S 15/62
See application file for complete search history.

(56) References Cited

U.S. PATENT DOCUMENTS

| 5,913,823 | A | 6/1999 | Hedberg | |
| 6,104,670 | A | 8/2000 | Hossack | |
| 6,222,795 | B1 | 4/2001 | Hossack | |
| 2006/0052699 | A1* | 3/2006 | Angelsen | A61B 8/483 600/437 |
| 2010/0069751 | A1* | 3/2010 | Hazard | G01S 7/52042 600/438 |
| 2012/0253194 | A1* | 10/2012 | Tamura | G01S 7/52071 600/438 |
| 2015/0201905 | A1* | 7/2015 | Ivancevich | A61B 8/461 600/438 |
| 2018/0228471 | A1* | 8/2018 | Park | A61B 8/469 |
| 2019/0298312 | A1* | 10/2019 | Labyed | A61B 8/5207 |

FOREIGN PATENT DOCUMENTS

EP   2881041 A1   6/2015

OTHER PUBLICATIONS

Zheng, et al., "Ultrasonic Vibrometry Using Orthogonal-Frequency-Based Vibration Pulses", IEEE Transactions on Ultrasonics, Ferroelectrics, and Frequency Control, IEEE, US, vol. 60, No. 11, Nov. 2013, pp. 2359-2370. (Year: 2013).*

(Continued)

*Primary Examiner* — Pascal M Bui Pho
*Assistant Examiner* — Taylor Deutsch

(57) ABSTRACT

Asymmetry is provided for the pushing pulse in acoustic radiation force impulse (ARFI) imaging. MI is based on the negative pressure. By increasing the positive pressure more than the negative pressure, the magnitude of displacement may be increased without exceeding the MI limit. Similarly, negative voltages depole while positive do not, so using an ARFI or pushing pulse with asymmetric positive-to-negative peak pressures or voltages allows for generation of greater magnitude of displacement without harm to the transducer.

18 Claims, 3 Drawing Sheets

(56) References Cited

OTHER PUBLICATIONS

"Ultrasound vibrometry using orthogonal-frequency-based vibration pulses," IEEE Transactions on Ultrasonics, Ferroelectrics and Frequency Control, IEEE, US, vol. 60, No. 11, Nov. 1, 2013, pp. 2359-2370.
International Search Report Dated Jun. 9, 2020 for corresponding International Application No. PCT/US2020/016918.

* cited by examiner

ASYMMETRY FOR ACOUSTIC RADIATION FORCE IMPULSE

BACKGROUND

The present embodiments relate to acoustic radiation force impulse (ARFI) or elastography imaging. By transmitting an ARFI as a pushing pulse, ultrasound may be used to displace tissue directly or through generation of a shear or longitudinal wave. The displacement resulting from the pushing pulse may be measured using further ultrasound scanning. Elasticity, shear, or other types of parametric imaging measure tissue characteristics based on the displacement caused by the ARFI.

ARFI-based ultrasound imaging is limited by low displacement signals. The induced displacement is directly related to the applied force and thus the local acoustic intensity. This intensity is often restricted by regulatory limits. One regulatory limit, the Mechanical Index (MI), is defined as:

$$MI = \frac{P_{max}^-}{\sqrt{f_c}},$$

where $P_{max}^-$ is the peak rarefactional (negative) pressure and $f_c$ is the center frequency of the transmit. MI is restricted to a maximum value of 1.9, and many ultrasound systems use MI of about 1.4 to account for transducer and system variability. MI acts to limit the overall output, thus limiting the displacement magnitude. Additionally, transducers are limited by a maximum voltage that can be applied across the piezoelectric elements to ensure transducer safety. If the voltage applied is too negative, then the transducer may depole or lose its ability to convert electrical to mechanical energy.

To increase displacement if limited by MI or ceiling voltage, longer duration pushing pulses are used. However, the maximum duration of a given transmit event is limited by the physics of elastography and stiffness of the tissue being imaged.

SUMMARY

By way of introduction, the preferred embodiments described below include methods, instructions, and systems for asymmetry in acoustic radiation force impulse (ARFI) scanning. MI is based on the negative pressure. By increasing the positive pressure more than the negative pressure, the magnitude of displacement may be increased without exceeding the MI limit. Similarly, negative voltages depole while positive do not, so using an ARFI or pushing pulse with asymmetric positive-to-negative peak pressures or voltages allows for generation of greater magnitude of displacement without harm to the transducer.

In a first aspect, a method is provided for acoustic radiation force impulse scanning by an ultrasound system. The ultrasound system transmits from an ultrasound transducer a transmit beam as an acoustic radiation force impulse where an absolute value of a peak positive pressure is at least 1.2 times an absolute value of a peak negative pressure at a focal location of the transmit beam. The ultrasound system tracks, using the ultrasound transducer, displacement of tissue where the displacement is in response to the acoustic radiation force impulse. An image is generated as a function of the displacement of the tissue.

In a second aspect, an ultrasound system is provided for acoustic radiation force impulse scanning. An ultrasound transducer is provided for transmitting an acoustic radiation force impulse in a patient. A transmit beamformer is configured to generate electrical waveforms for the acoustic radiation force impulse. The electrical waveforms as generated have multiple cycles and a ratio of positive to negative peak voltage of at least 1.5 for at least about ½ of the cycles. A receive beamformer is configured to output data representing a spatial location as a function of received acoustic signals responsive to motion of the tissue due to the acoustic radiation force impulse. A processor is configured to estimate displacement of the tissue in the patient over time as a function of the output data. A display is operable to display an image where the image is a function of the displacement.

In a third aspect, a method is provided for imaging by an ultrasound system. The ultrasound system transmits acoustic waveforms from elements of an ultrasound transducer. The acoustic waveforms at the elements have a beamformer generated asymmetry between the peak positive and peak negative pressures for at least ⅓ of cycles. The acoustic waveforms cause displacements of tissue. Shear wave imaging is performed from the displacements.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

An asymmetric pushing pulse is used for radiation force-based ultrasound Imaging. Low displacement is solved by increasing acoustic output while maintaining safety for the patient (i.e., staying within regulatory limits) and reliability and performance of transducer hardware (i.e., avoiding depoling and other degradation issues associated with high drive voltage).

The pushing pulse is modified to allow for the same peak negative voltage and pressure while increasing the acoustic intensity. The safety and reliability limits in both voltage and pressure are more stringent on the negative side of a pulse than the positive. Since the peak negative voltage and pressure are related to transducer safety and patient safety, keeping these values within the limits while increasing acoustic intensity through increasing positive pressure and voltage allows for more displacement signal. Driving with a greater voltage in the positive direction will not result in depoling and may even result in a depoling of previously depoled elements. In reaching MI limits or ceiling voltage limits, the peak negative voltage applied to the transducer is the limiting factor, at least initially. The intensity of the pushing pulse is increased utilizing an asymmetric transmit pulse that has higher absolute positive voltage/pressure than negative voltage/pressure. An asymmetric transmit pulse may increase local acoustic intensity, so the displacement signal is higher in radiation force-based imaging.

Figure 1:
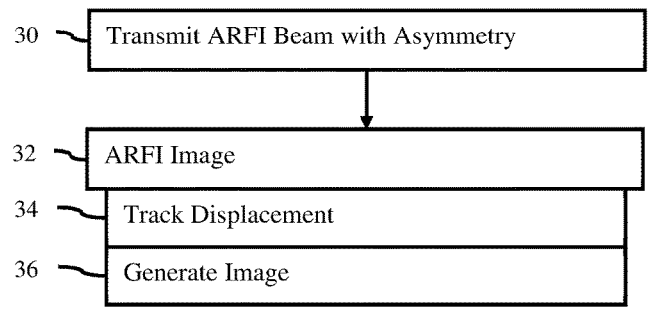
FIG. 1 is a flow chart diagram of one embodiment of a method for ARFI imaging with asymmetric pushing pulses.

FIG. 1 shows a method for imaging by an ultrasound system. ARFI scanning is used by the ultrasound system to image tissue response to displacement. A pushing pulse ultrasound transmission is used to generate tissue displacement. The pushing pulse uses an asymmetric transmit waveform, which has a higher positive peak pressure than negative peak pressure. This allows for greater magnitude of displacement while satisfying MI and transducer limits.

Figure 4:
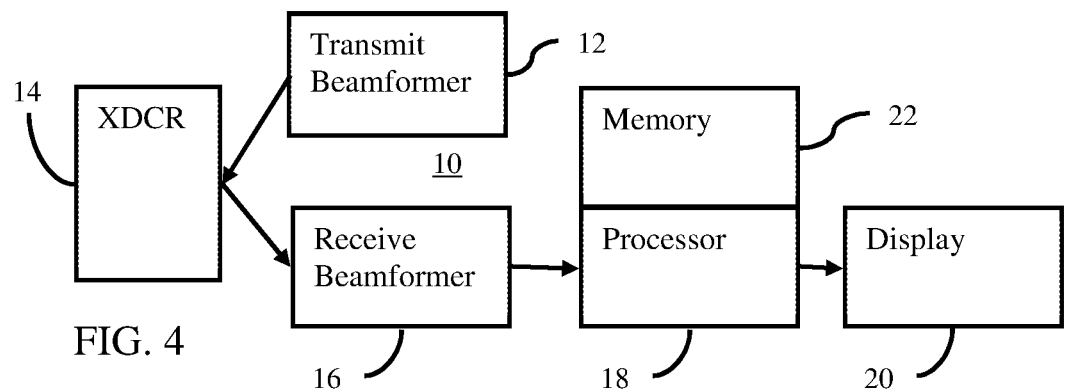
FIG. 4 is a block diagram of one embodiment of an ultrasound system for an asymmetric pushing pulse in elasticity imaging.

The method is implemented by the ultrasound system of FIG. 4 or a different system. For example, a transmit beamformer is used to generate element waveforms, and a transducer generates acoustic waveforms from the element waveforms. The acoustic waveforms constructively interfere in the patient as an ARFI transmit beam. The transmit beamformer and a receive beamformer are used to track displacement in tissue caused by the ARFI transmit beam. The ultrasound system generates an image from the displacement.

Additional, different, or fewer acts may be provided. For example, the method is performed without generating an image in act 36. In yet another example, acts for estimating tissue characteristics or properties from the displacements are provided. The acts are performed in the order described or shown (e.g., top to bottom or numerical), but may be performed in other orders.

In act 30, an acoustic radiation force impulse (ARFI) beam is transmitted. The beam has asymmetry between the positive and negative peak pressures. The transmit beamformer generates electrical waveforms for the elements of the transducers where the electrical waveforms have the asymmetry or may be combined electrically or acoustically to provide asymmetry. When applied to the elements, the elements generate acoustic waveforms at the faces of the elements. The acoustic waveforms have the asymmetry or may combine to provide the asymmetry. The acoustic waveforms constructively sum along a scan line and at the focus so that the transmit beam includes the asymmetry. An array of elements in an ultrasound transducer transmits the ARFI beam converted from the electrical waveforms. The acoustic energy with asymmetry of the pushing pulse is transmitted to the tissue in a patient.

The acoustic waveform of the beam is transmitted for generating a shear, longitudinal, or other wave as stress to displace tissue. The excitation is an ultrasound pushing pulse. The acoustic energy is focused to apply sufficient energy to cause generation of one or more waves travelling through the tissue from the focal location or locations. The acoustic waveform may itself displace the tissue.

The shear or longitudinal wave or waves are generated at the focal region and propagate laterally, axially, and/or in other directions from the focal region. The waves may travel in multiple directions. The waves reduce in amplitude as the waves travel through the tissue.

To generate the wave or to displace the tissue, high amplitude or power excitations are desired. For example, the excitation has a mechanical index of close to but not exceeding 1.9 at the focal location and/or in the field of view. To be conservative and account for probe variation, mechanical index of 1.4, 1.7, or other level may be used as the upper limit. Greater (e.g., MI exceeding 1.9) or lesser powers may be used.

The ARFI beam is transmitted with waveforms having any number of cycles. In one embodiment, one, most, or all the waveforms (e.g., electrical waveforms, element-level acoustic waveforms, or beam waveform) for a transmit event of a pushing pulse have 100-2,000 cycles. The number of cycles is tens, hundreds, thousands, or more for the continuous transmit waveforms applied to the elements of the array for the ARFI beam. Unlike imaging pulses that are 1-5 cycles, the ARFI pushing pulse has a greater number of cycles to generate sufficient stress to cause the wave (e.g., shear wave) for displacing tissue with an amplitude sufficient to detect. A pushing pulse beam of acoustic energy is transmitted. ARFI is transmitted from the array by application of the continuous transmit waveforms to the elements of the array over the period.

The length of the transmission in combination with the amplitude of the waveform provides acoustic power to the tissue. Since the asymmetry provides greater amplitude for the positive pressure or voltage, a waveform of the same duration provides greater power. This may allow for the pushing pulse to use fewer cycles while still providing sufficient or even greater power than without asymmetry. The greater acoustic power may cause greater tissue displacement, which may be more consistently and/or reliably measured with ultrasound scanning.

The waveforms applied to the elements are generated as continuous waveforms. Various waveforms may be used, such as square wave, sinusoidal wave, or other bipolar alternating waveform. The waveform does not have any extended periods of zero output other than to begin and end the waveform. An extended period is one or more cycles. There may be part of each cycle at zero, such as for a unipolar square wave, but another part of the cycle has non-zero (positive or negative) output per cycle.

The electrical waveform generated for each element in the aperture are square waves or sinusoidal waves. The generated electrical waveforms are applied to the elements in synchronization, resulting in generation of the ARFI transmit beam.

Each or at least some of the electrical waveforms for a given pushing pulse, ARFI beam, or transmit event have an absolute value of peak positive amplitude at least 1.2 times an absolute value of peak negative amplitude. The peak positive amplitude or voltage is greater than the peak negative amplitude or voltage. The absolute value of the positive peak magnitude is greater than the absolute value of the negative peak magnitude. Any ratio of the positive amplitude to the negative amplitude may be used, such as 1.2, 1.5, or 2.0. The ratio is at least 1.2, 1.5, or 2.0. The ratio may be higher as long as a total power limit (e.g., ISPTA) is not exceeded, such as a ratio of 10.

This ratio is provided for each cycle of the electrical waveform, as an average across all cycles, and/or for at least ⅓ of the cycles. For example, the ratio is provided for about ½ of the cycles where the electrical waveform is made from a phase aligned combination or superposition of a fundamental waveform (e.g., 4 MHz sinusoidal) and a second harmonic waveform (e.g., 8 MHz sinusoidal). "About" for the number of cycles is used to account for beginning and/or ending one or more cycles ringing or ramp up or down relative the steady state of the amplitude envelope.

Each electrical waveform is generated separately, but some waveforms may be generated together. The transmit beamformer or waveform generator generates the electrical waveforms. In one embodiment, a transmit beamformer having a capability to generate two or more transmit beams simultaneously is used. The electrical waveforms for one transmit beam are combined with the electrical waveforms for another transmit beam before application to the transducer or as part of application to the transducer. The two beams are colinear. The electrical waveforms combine or superpose in a way to have a greater positive amplitude than negative amplitude. For example, the zero-crossings of a fundamental waveform at one center frequency and another waveform at a second harmonic frequency are aligned to provide the asymmetry. Other harmonics may be used. In other embodiments, the electrical waveform for an element is generated by switches and/or pulsers. A positive voltage source with a greater amplitude is used with a negative voltage source with a lesser amplitude. Switches are controlled to switch between the positive and negative voltage sources. In yet other embodiments, a sinusoidal with the asymmetry is generated, such as from memory or digital-to-analog conversion. Other electrical waveform generation may be used.

In other embodiments, different electrical waveforms are generated for different elements. The electrical waveforms may not include asymmetry but are at different frequencies and/or phasing so that asymmetry is provided for the transmit beam at the focal location based on the constructive summation of the acoustic waveforms.

The electrical waveforms include both positive and negative components. The amplitude of the positive component is greater than the amplitude of the negative component. The amount of positive power (e.g., integral of positive voltage) may be greater than the amount of negative power (e.g., integral of the negative voltage) by the ratio.

The electrical waveforms for a transmit aperture are applied to the elements of the transducer. The elements convert the electrical waveforms to acoustic energy. At the face of each element, an acoustic waveform is generated to transmit the acoustic waveform into the patient. Even with any non-linear operation of the element, the acoustic waveforms of the transmit aperture have the asymmetry, such as a ratio of 1.5 for at least about ½ or all the cycles or a ratio of 2.0 for about ½ of the cycles. Alternatively, the electrical waveforms and/or corresponding element-based acoustic waveforms are symmetrical but constructively combine to provide asymmetry along the transmit beam.

In one embodiment, the acoustic waveforms have a beamformer generated asymmetry between the peak positive and peak negative pressures. The transmit beamformer generates the electrical waveforms to have the asymmetry with or without consideration for any non-linear interactions or propagation of the electrical and/or acoustic energy. The asymmetry is generated intentionally rather than as a result of transmission.

The acoustic waveforms propagate from the elements. The acoustic waveforms from the elements constructively interfere along the transmit scan line, such as at the focal location or region. At the focal location, the constructive sum of the acoustic waveforms provides the transmit beam with asymmetry. For example, the absolute value of a peak positive pressure is at least 1.2, 1.5, or 2.0 times an absolute value of a peak negative pressure at a focal location of the transmit beam. The ratio may be 5 or more (e.g., 10). This ratio is provided as an average, for all, or for any number (e.g., ⅓ or more or about ½) of the cycles.

Figure 2:
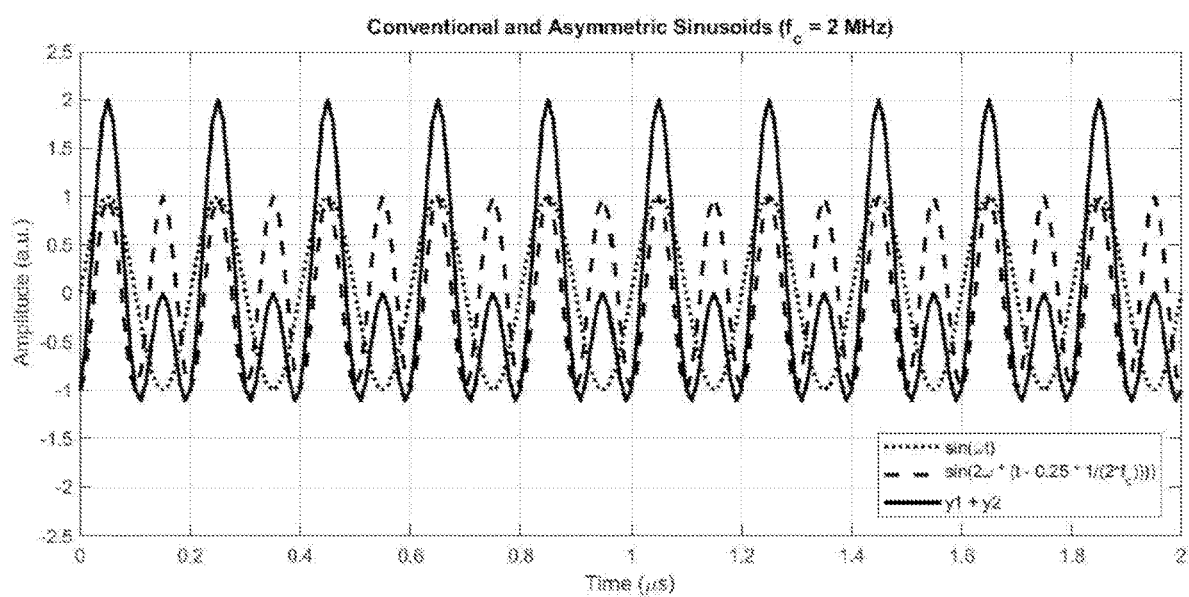
FIGS. 2 and 3 are example asymmetric pushing pulse waveforms.

In one embodiment, the asymmetry at the focal location is based on the transmit beam having fundamental frequency and second harmonic frequency components aligned to form the ratio of absolute values of the peak positive and peak negative pressures. FIG. 2 shows one example of an asymmetric transmit pulse that is a combination of a sinusoid with a phase-shifted sinusoid of twice the frequency. The peak negative amplitude of the pushing pulse is slightly greater in absolute value than either the waveform at the fundamental frequency or the waveform at the second harmonic frequency. The peak positive amplitude is about twice as high as either of the conventional sinusoids (i.e., the fundamental and second harmonic waveforms). "About" when referring to the ratio, accounts for waveform generation tolerance and/or propagation distortion or attenuation. In other embodiments, the fundamental and second harmonic have different relative amplitudes. The peak positive and peak negative of the fundamental and harmonic waveforms is the same but may not be equal in other embodiments.

If the transducer bandwidth includes both transmit frequencies, the output pulse is appropriately generated. For example, the fundamental component is at 1-5 MHz and the second harmonic component is at 2-10 MHz. Single crystal piezoelectric elements may provide the bandwidth for transmission of both fundamental and second harmonic waveforms. Other types of elements may be used.

Figure 3:
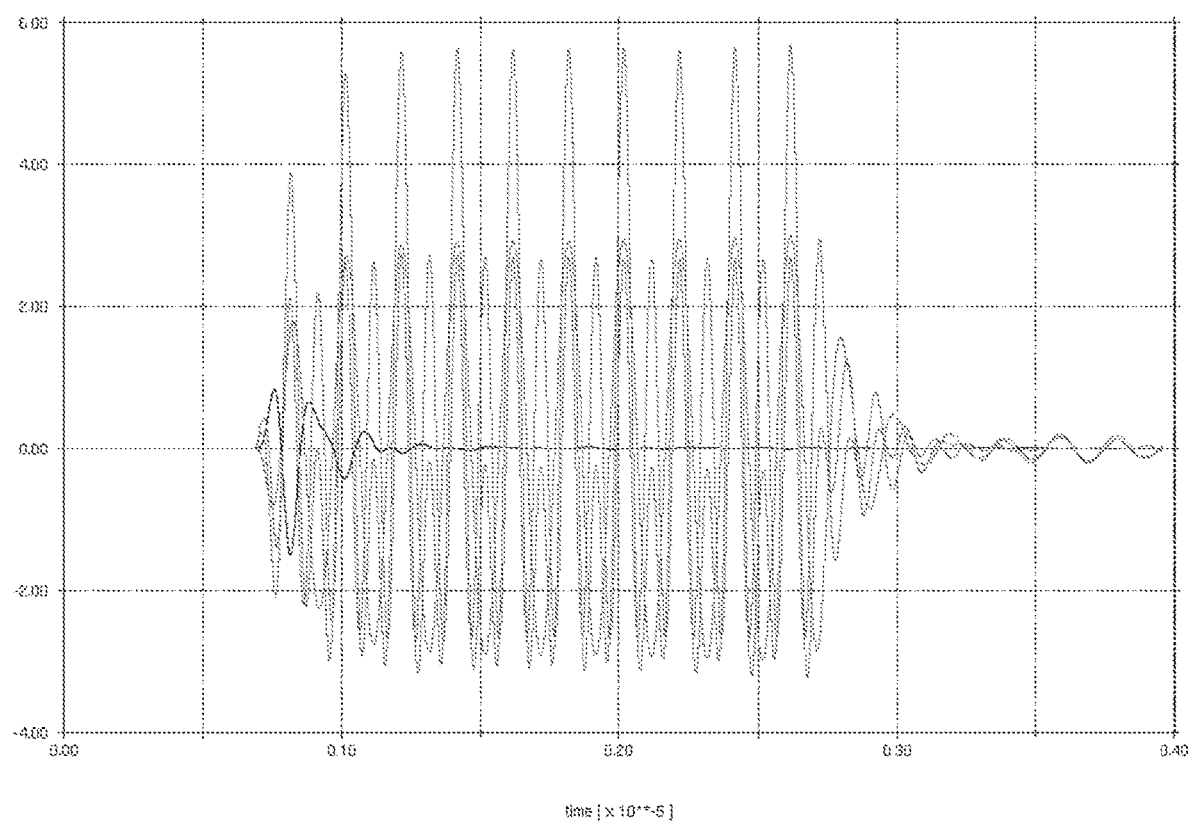

FIG. 3 shows a simulation using a model of a breast transducer with a bandwidth that contains both 5 MHz and 10 MHz in the −6 dB bandwidth of the transducer. The asymmetric waveform is an acoustic waveform transmitted by the transducer. In this case, the MI is slightly higher than transmitting a waveform for just the fundamental component. The acoustic intensity, defined as the integral of the pressure squared, doubles due to the asymmetry from the superposition of the fundamental and second harmonic components. The displacement magnitude would double as well, leading to improved imaging capability in ARFI mode.

In act 32 of FIG. 1, the ultrasound system performs shear wave imaging from the ARFI-induced displacement. The tissue displaces due to the ARFI transmit beam. The displacement has a greater magnitude due to asymmetry as compared to symmetric positive and negative pressures or amplitudes given a same MI. Any type of elasticity or ARFI imaging may be used.

For imaging, the ultrasound system tracks the displacement in act 34 and generates an image based on the displacement in act 36. In act 34, the ultrasound system, using the beamformer, transducer, and an image processor, tracks displacements in the tissue caused by the wave generated from the ARFI transmit beam. The transmit beamformer generates transmit waveforms, the transducer converts the waveforms to transmit beams and converts echoes of the transmit beams to receive signals, the receive beamformer forms receive beams from the receive signals, and the image processor correlates receive beams or data from the receive beams to determine displacements.

The tissue response is a function of the wave created by the ARFI beam and the tissue characteristics. The displacement of the tissue over time may be expressed as a convolution of the waveform and the tissue characteristics or response. The tissue response reflects viscoelastic properties of the tissue. To measure the viscoelastic properties, the displacement of the tissue over time in response to the pushing pulse is measured. The displacement of the tissue caused by the created wave or the ARFI pulse itself is determined over time. As the wave passes a given location, the tissue displaces by an amount or distance that increases to a peak amount and then decreases as the tissue returns to rest.

The displacement is calculated as a function of time. The tissue is scanned multiple times to determine the displacement, such as scanning a region at least ten times to determine displacements at nine different times. The tissue is scanned using any imaging modality capable of scanning for displacement during the tissue's response to the pushing waveform. The scan occurs over a range of times where the desired waveform (e.g., shear wave) would be passing through the tissue.

For ultrasound scanning, the wave is detected at locations adjacent to and/or spaced from the focal region for the ARFI pushing pulse. To detect tissue response to waves in a region of interest, transmissions are made to the region. These other transmissions are for detecting the waves or displacement rather than causing the wave or displacement. The transmissions for detection may have lower power and/or short pulses (e.g., 1-5 carrier cycles) and use the same or different scan line as the ARFI beam. The transmissions for detection may have a wider beam profile along at least one dimension, such as laterally, for simultaneously forming receive samples along a plurality of scan lines.

The ARFI transmit beam is not used for receiving echoes. The frequency of the tracking waveforms used for transmit and the frequency for receive are independent of the frequencies used for the ARFI beam. For example, the ARFI has fundamental and second harmonics at 3 and 6 MHz while the tracking beams are B-mode beams with a center transmit frequency of 2 MHz and a receive frequency of 2 MHz or 4 MHz harmonic. Since the ARFI is not used for receiving, the signal from the ARFI does not or has limited interference with the receive signals for tracking. The tracking transmissions do not have asymmetry in the positive and negative peaks but may have asymmetry.

The wave or displacement may be monitored in one, two, or more directions. A region of interest is monitored to detect the wave. The region of interest is any size. Laterally spaced locations are monitored for shear wave imaging. The displacements are tracked at each of a plurality of laterally spaced locations for one or more depths. Alternatively, the displacements for a single location are tracked.

The detection region is monitored by ultrasound. The monitoring is performed for any number of scan lines. For example, four, eight, or more receive beams are formed in response to each monitoring transmission. After transmitting the ARFI excitation to generate the wave or displacement, B-mode transmissions are performed repetitively along one or more transmit scan lines and receptions are performed along corresponding receive scan lines. In other embodiments, only a single receive beam or other numbers of receive beams are formed in response to each transmission. Some of the ultrasound data, such as at the beginning or end of the repetitions, may not be responsive to the wave or displacement.

An image processor calculates the displacements from the ultrasound scan data (e.g., beamformed samples or B-mode detected data). The tissue moves between two scans. The data of one scan is translated in one, two, or three dimensions relative to the data in the other scan. For each possible relative position, an amount of similarity is calculated for data around a location. The amount of similarity is determined with correlation, such as a cross-correlation. A minimum sum of absolute differences or other function may be used. The spatial offset with the highest or sufficient correlation indicates the amount and direction of displacement for a given location. In other embodiments, a phase offset of data received from different times is calculated. The phase offset indicates the amount of displacement. In yet other embodiments, data representing a line (e.g., axial) at different times is correlated to determine a shift for each of a plurality of depths along the line.

Displacements are determined for a given location at different times, such associated with sequential scans. The displacement is determined with respect to an initial or reference frame of scan data (i.e., cumulative displacement). Alternatively, the displacement is determined from the immediately prior frame of scan data, such assigning the previous frame as the reference on an ongoing basis (i.e., incremental displacement). The temporal profile for a given location indicates displacement caused by the wave over time. Alternatively, a displacement at a given time is determined.

The displacement information, with or without a time profile, is used to determine a characteristic of the tissue. The characteristic is determined at one location or for each of multiple locations. Any characteristic may be determined, such as an elasticity, strain, shear velocity, longitudinal wave velocity, modulus, or other viscoelastic property. The displacements themselves, such as the magnitude of the displacement, may be used to represent the tissue property.

In act 36 of FIG. 1, an image is generated. The image represents the tissue characteristic or property. The image is a function of the displacement or displacements. Using the displacements themselves or a characteristic derived from the displacements (e.g., shear modulus or velocity), information to be displayed is calculated. For example, a numerical or textual indication of the property may be displayed. In other embodiments, a plot and/or fit line and slope value are output. For example, displacement over time is displayed for each of one or more locations. The viscoelastic property is communicated to the user in the image. The image may be a graph, such as a plot of values as a function of location.

The image may include a one, two, or three-dimensional representation of the property, displacement, or other wave information as a function of space or location. For example, the shear velocities throughout a region are displayed. Shear velocity values modulate color for pixels in a region in a gray-scale modulated B-mode image. The image may represent displacement information, such as shear or moduli (e.g., the shear moduli) for different locations. The display grid may be different from the scan grid and/or grid for which displacements are calculated. Color, brightness, luminance, hue, or other characteristic of pixels is modulated as a function of the information derived from the displacements.

In other embodiments, the displacements are used for shear wave velocity imaging. The distribution of shear velocities in a two or three-dimensional region are determined and mapped to image values. In another embodiment, shear wave velocity point quantification is performed. The value of the shear wave velocity at a location is displayed as text or a numerical value. Due to the asymmetry-caused greater displacement, the region represented may be larger and/or the displacements more reliably detected, resulting in better accuracy and/or more diagnostic image information.

FIG. 4 shows one embodiment of an ultrasound system 10 for ARFI scanning. Ultrasound generates tissue displacement, such as through creation of a shear or longitudinal wave, and scan data responsive to the tissue responding to the displacement is used to determine a property. For increased displacement, the ARFI is transmitted with asymmetry between the positive and negative peaks. The increased displacement may be more easily and/or broadly tracked.

The system 10 is a medical diagnostic ultrasound imaging system. In alternative embodiments, the system 10 is a personal computer, workstation, PACS station, or other arrangement at a same location or distributed over a network for real-time or post acquisition imaging. Data from a beamformer-performed ultrasound scan is available through a computer network or memory for processing by the computer or other processing device.

The system 10 implements the method of FIG. 1 or other methods. The system 10 includes a transmit beamformer 12, a transducer 14, a receive beamformer 16, an image processor 18, a display 20, and a memory 22. Additional, different or fewer components may be provided. For example, a user input is provided for manual or assisted designation of a region of interest for which information is to be obtained or for entry of an application, type of tissue, and/or setting of level of asymmetry (e.g., setting the ratio).

The transmit beamformer 12 is an ultrasound transmitter, memory, pulser, waveform generator, analog circuit, digital circuit, or combinations thereof. The transmit beamformer 12 is configured to generate waveforms for a plurality of channels with different or relative amplitudes, delays, and/or phasing. The waveforms include asymmetry or frequency and amplitude combinations to provide asymmetry at the focal region. For a given ARFI (e.g., 100-1000 cycles), the asymmetry is provided for about ⅓, ½, all or other number of the cycles. This asymmetry is performed for all or a sub-set of the channels of the transmit beamformer 12.

In one embodiment, the transmit beamformer 12 includes different voltage sources, multiple simultaneous transmit beam capability (e.g., two channels per element), pulsers, switches, memories, digital-to-analog converters, or other waveform generators for generating asymmetric waveforms or waveforms that may be combined to form asymmetry. The combination occurs electrically before or at the transducer or acoustically after the transducer.

The transmit beamformer 12 is configured to generate electrical waveforms with or used to cause acoustic waveforms with greater peak positive amplitude than negative amplitude. For example, the ratio of positive to negative peak voltage of at least 1.5 for at least about ½ of the cycles. In one embodiment, the ratio is at least 2.0, such as 2.0-10.0. In another embodiment, the ratio is about 2.0 where fundamental and second harmonic electrical waveforms with a same amplitude (i.e., equal positive and negative peak amplitudes or voltages within and between the fundamental and harmonic waveforms) are combined. The electrical waveforms are aligned in phase so that superposition causes a greater positive peak than negative peak in the combination. The combination is asymmetric and applied to the transducer 14. The relative amplitudes between the waveforms may be set to provide the desired ratio of asymmetry in the positive to negative peaks.

The transmit beamformer 12 connects with the transducer 14, such as through a transmit/receive switch. Upon transmission of acoustic waves from the transducer 14 in response to the generated waveforms, one or more beams are formed during a given transmit event. At least one beam is an ARFI pulse with asymmetry in the positive-to-negative pressures. For scanning tissue displacement, a sequence of other transmit beams are generated after the ARFI is transmitted. The other transmit beams are symmetric in peak pressures but may be asymmetric in peak pressures. The sequence of transmit beams scans a one, two or three-dimensional region. Sector, Vector® (sector with the origin behind the array), linear, or other scan formats may be used. The same region is scanned multiple times. The scanning by the transmit beamformer 12 occurs after transmission of the ARFI pulse. The same elements of the transducer 14 are used for both scanning and displacing tissue, but different elements, transducers, and/or beamformers may be used.

The transducer 14 is a 1-, 1.25-, 1.5-, 1.75- or 2-dimensional array of piezoelectric (PZT) or capacitive membrane elements. In one embodiment, the elements are single crystal PZT elements. The transducer 14 includes a plurality of elements for transducing between acoustic and electrical energies. For example, the transducer 14 is a one-dimensional PZT array with about 64-256 elements.

The transducer 14 connects with the transmit beamformer 12 for converting electrical waveforms into acoustic waveforms and connects with the receive beamformer 16 for converting acoustic echoes into electrical receive signals. The transducer 14 transmits the ARFI. The transmit beam of the ARFI is focused at a tissue region or location of interest in the patient. The acoustic waveform is generated in response to applying the electrical waveforms to the transducer elements. The ARFI causes tissue displacement, either directly or through generation of a wave (e.g., shear wave).

For scanning with ultrasound to detect displacement (tracking), the transducer 14 transmits acoustic energy based on further waveforms from the transmit beamformer 12 and receives echoes. Receive signals are generated by the receive beamformer 16 in response to ultrasound energy (echoes) impinging on the elements of the transducer 14.

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to each transmission for detection. Dynamic focusing on receive may be provided. The receive beamformer 16 outputs data representing one or more spatial locations using the received acoustic signals. Relative delays and/or phasing and summation of signals from different elements provide beamformation. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental, or another band.

The receive beamformer 16 outputs beam summed data representing one or more spatial locations. Data for a single location, locations along a line, locations for an area, or locations for a volume are output. The data may be for different purposes. For example, different scans are performed for B-mode or tissue data than for shear wave detection. Alternatively, the scan for B-mode imaging is used for determining tissue displacements. The receive beamformer 16 outputs data representing spatial locations where the data is a function of received acoustic signals responsive to the tissue as moving due to the ARFI. The receive beamformer 16 does not operate while direct echoes from the ARFI impinge on the transducer 14, so the receive beamformer 16 is configured to output the data without acoustic echoes from the ARFI.

The processor 18 is a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, combinations thereof or other now known or later developed device for detecting and processing information from beamformed ultrasound samples. In one embodiment, the processor 18 includes one or more detectors and a separate processor. The separate processor is a control processor, general processor, digital signal processor, graphics processing unit, application specific integrated circuit, field programmable gate array, network, server, group of processors, data path, combinations thereof or other now known or later developed device for determining displacement and/or calculating tissue properties. The processor 18 is configured by software, firmware, and/or hardware to perform the acts.

In one embodiment, the processor 18 estimates tissue displacement over time as a function of the output data from the receive beamformer 16. The displacements are estimated as a profile or data representing a curve of magnitude of displacement as a function of time. The displacement profile may be obtained by correlating or otherwise determining level of similarity between reference data and data obtained to represent the tissue at a different time. The displacement profile is determined for each location. In alternative embodiments, a displacement at a given time is determined for each of one or more locations.

The processor 18 is configured to calculate tissue characteristics from the displacements of the tissue over time or from a displacement at a time. For example, a shear velocity is calculated from the displacement over time. The amount of displacement identifies a time of occurrence of the shear wave. The distance from the origin of the shear wave (e.g., ARFI focal location) divided by the time provides velocity. Relative phasing of displacement profiles over different locations may be used to determine the shear velocity.

In one embodiment, the processor 18 calculates viscosity and/or modulus. The processor 18 may calculate other properties, such as strain or elasticity. In yet other embodiments, the processor 18 determines the maximum displacement or other characteristic of displacement or the displacement profile as the characteristic.

The processor 18 generates and outputs image or display values mapped from the property to the display 20. For example, the shear modulus or other value is determined. A text or numerical indication of the property is displayed to the user. A graph of the property over time may be displayed.

In one embodiment, the property (e.g., shear wave velocity) is displayed as a function of location. Displacements for a number of locations are available in response to an ARFI pulse. A one, two, or three-dimensional distribution of those locations provides a corresponding spatial distribution of estimated velocity or property. For a representation of the tissue, the magnitude of the tissue characteristic modulates the color, hue, brightness, and/or other display characteristic for different pixels representing a tissue region. The processor 18 determines a pixel value (e.g., RGB) or a scalar value converted to a pixel value. The image is generated as the scalar or pixel values. The image may be output to a video processor, look-up table, color map, or directly to the display 20.

The processor 18 and the transmit beamformer 12 operate pursuant to instructions stored in the memory 22 or another memory. The instructions configure the processor 18 and/or the transmit beamformer 12 for operation by being loaded into a controller, by causing loading of a table of values (e.g., beamformer control table), and/or by being executed. The transmit beamformer 12 is configured by the instructions to cause generation of an ARFI beam with asymmetry in the positive-to-negative peak amplitudes. The processor 18 is programmed for measuring tissue displacement and generating an image.

The memory 22 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts, or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 20 is a CRT, LCD, projector, plasma, or other display for displaying two-dimensional images or three-dimensional representations. The display 20 displays one or more images representing the tissue characteristic or other information derived from a displacement or displacements (i.e., image representing tissue reaction to the ARFI). As an example, a two-dimensional image or three-dimensional representation of displacement or tissue characteristics as a function of location is displayed. Alternatively or additionally, the image is a graph, a number, or text representation of a value or graph. For example, a shear velocity, shear modulus, strain, elasticity or other value is displayed as the image or an annotation on a B-mode image.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for acoustic radiation force impulse scanning by an ultrasound system, the method comprising:
transmitting, by the ultrasound system and from an ultrasound transducer, a transmit beam as an acoustic radiation force impulse, wherein the transmit beam is generated with a plurality of element waveforms that are continuous over time, wherein each of the plurality of the element waveforms comprise a plurality of cycles, wherein an absolute value of a peak positive pressure of the transmit beam is at least 1.2 times an absolute value of a peak negative pressure of the transmit beam within the same cycle at a focal location of the transmit beam, and wherein more than one of the plurality of cycles of each of the plurality of the element waveforms have an absolute value of peak positive amplitude of the element waveform of at least 1.2 times an absolute value of peak negative amplitude of the element waveform within the same cycle;

tracking, by the ultrasound system using the ultrasound transducer, displacement of tissue, the displacement being in response to the acoustic radiation force impulse; and generating an image, the image being a function of the displacement of the tissue.

2. The method of claim 1 wherein the transmitting comprises transmitting the transmit beam where the absolute value of the peak positive pressure is at least 2.0 times the absolute value of the peak negative pressure within the same cycle.

3. The method of claim 1 wherein the transmitting comprises transmitting with each of the plurality of the element waveforms having one hundred or more cycles with at least $\frac{1}{3}$ of the one hundred or more cycles having the absolute value of the peak positive amplitude of the element waveform at least 1.2 times the absolute value of the peak negative amplitude of the element waveform within the same cycle.

4. The method of claim 1 wherein the generating comprises generating, for each of a plurality of elements of a transmit aperture of the ultrasound transducer, a first waveform at a center frequency and a second waveform at a second harmonic frequency of the center frequency and forming one of the plurality of the element waveforms for each of the elements of the plurality of the elements by combination of the first and second waveforms such that every other cycle of the plurality of the cycles has the peak positive amplitude of the element waveform at least 1.2 times the absolute value of the peak negative amplitude of the element waveform within the same cycle.

5. The method of claim 1 wherein the transmitting comprises transmitting the transmit beam having fundamental frequency and second harmonic frequency components aligned to form the absolute value of the peak positive pressure at the at least 1.2 times the absolute value of the peak negative pressure within the same cycle at the focal location.

6. The method of claim 1 wherein the tracking comprises tracking a shear wave generated by the acoustic radiation force impulse.

7. The method of claim 1 wherein the generating comprises generating the image with pixels modulated as a function of the displacement of the tissue in a two or three-dimensional field.

8. An ultrasound system for acoustic radiation force impulse scanning, the system comprising:

an ultrasound transducer for transmitting an acoustic radiation force impulse in a patient;

a transmit beamformer configured to generate a plurality of electrical waveforms for the acoustic radiation force impulse, each of the electrical waveforms of the plurality of the electrical waveforms as generated having multiple cycles and a ratio of positive to negative peak voltage within the same cycle of at least 1.5 for at least about $\frac{1}{2}$ of the cycles;

a receive beamformer configured to output data representing a spatial location as a function of a plurality of received acoustic signals responsive to motion of tissue due to the acoustic radiation force impulse;

a processor configured to estimate displacement of the tissue in the patient over time as a function of the output data; and a display operable to display an image, the image being a function of the displacement.

9. The ultrasound system of claim 8 wherein the transmit beamformer is configured to generate each of the electrical waveforms of the plurality of the electrical waveforms with the ratio being at least 2.0.

10. The ultrasound system of claim 8 wherein the transmit beamformer is configured to generate each of the electrical waveforms of the plurality of the electrical waveforms with the ratio being about 2.0.

11. The ultrasound system of claim 8 wherein the transmit beamformer is configured to generate one of the electrical waveforms of the plurality of the electrical waveforms for each element of a plurality of elements of the ultrasound transducer, each of the electrical waveforms of the plurality of the electrical waveforms being a superposition of a fundamental waveform and a harmonic waveform aligned in phase to form the ratio.

12. The ultrasound system of claim 8 wherein the receive beamformer is configured to output the data representing the spatial location and other spatial locations, the processor is configured to estimate the displacement of the tissue in the patient over time for each of the spatial location and other spatial locations, and wherein the image represents a two or three-dimensional distribution of tissue reaction to the acoustic radiation force impulse.

13. The ultrasound system of claim 8 wherein the image comprises a shear wave image.

14. A method for imaging by an ultrasound system, the method comprising:

transmitting, by the ultrasound system, a plurality of acoustic waveforms from a plurality of elements, respectively, of an ultrasound transducer, each of the acoustic waveforms of the plurality of the acoustic waveforms comprising a plurality of cycles and having a beamformer generated asymmetry between an absolute peak positive pressure and an absolute peak negative pressure within the same cycle for at least $\frac{1}{2}$ of the plurality of the cycles, the plurality of the acoustic waveforms causing a plurality of displacements of tissue; and shear wave imaging from the plurality of the displacements.

15. The method of claim 14 wherein the shear wave imaging comprises tracking, by the ultrasound system using the ultrasound transducer, the plurality of the displacements of the tissue and generating an image from the plurality of the displacements.

16. The method of claim 14 wherein the transmitting comprises transmitting with the acoustic waveforms of the plurality of acoustic waveforms having a ratio of the absolute peak positive pressure to the absolute peak negative pressure within the same cycle of at least 1.5 for the at least $\frac{1}{2}$ of the plurality of the cycles.

17. The method of claim 14 wherein the transmitting comprises transmitting with the acoustic waveforms of the plurality of acoustic waveforms having a ratio of the absolute peak positive pressure to the absolute peak negative pressure within the same cycle of at least 2 for about $\frac{1}{2}$ of the plurality of the cycles, the beamformer generated asymmetry formed by combination of phase-aligned fundamental and second harmonic electrical waves.

18. The method of claim 14 wherein the transmitting comprises transmitting with superposition of a plurality of separately generated electrical waveforms.

\* \* \* \* \*